(12) United States Patent
Wu et al.

(10) Patent No.: US 11,478,756 B2
(45) Date of Patent: Oct. 25, 2022

(54) DEVICE FOR INCUBATING AND WASHING MEMBRANE/GEL AND METHOD USING THEREOF

(71) Applicants: Rongrong Wu, El Sobrante, CA (US); Guofu Wang, Wuhan (CN); Suheng Liu, Wuhan (CN)

(72) Inventors: Rongrong Wu, El Sobrante, CA (US); Guofu Wang, Wuhan (CN); Suheng Liu, Wuhan (CN)

( * ) Notice: Subject to any disclaimer, the term of this patent is extended or adjusted under 35 U.S.C. 154(b) by 185 days.

(21) Appl. No.: 16/699,011

(22) Filed: Nov. 28, 2019

(65) Prior Publication Data

US 2021/0162349 A1    Jun. 3, 2021

(51) Int. Cl.
| | |
|---|---|
| B01D 65/02 | (2006.01) |
| G01N 1/34 | (2006.01) |
| B08B 3/04 | (2006.01) |
| B08B 3/08 | (2006.01) |
| C12M 1/00 | (2006.01) |

(52) U.S. Cl.
CPC ............... *B01D 65/02* (2013.01); *B08B 3/04* (2013.01); *G01N 1/34* (2013.01); *B08B 3/08* (2013.01); *C12M 41/14* (2013.01); *C12M 45/00* (2013.01)

(58) Field of Classification Search
CPC ... B01D 65/02; B08B 3/04; B01L 9/00; B01L 9/52
See application file for complete search history.

(56) References Cited

U.S. PATENT DOCUMENTS

| | | | | |
|---|---|---|---|---|
| 5,816,410 | A * | 10/1998 | Nyseth | H01L 21/67369 206/711 |
| 2013/0203072 | A1 * | 8/2013 | Tian | B01L 3/5025 435/7.1 |
| 2015/0285790 | A1 * | 10/2015 | Tian | B01L 3/508 422/554 |

* cited by examiner

Primary Examiner — Natasha N Campbell
(74) Attorney, Agent, or Firm — Feng Tian (57) ABSTRACT

The present disclosure provides devices, machines and methods for incubating or washing a biological sample membrane or gel automated processing of biological samples. This disclosure provides a device comprising a washing cassette, a sample holder, a poking gear and a washing basin assembly. The disclosure also provides machines comprising the device and methods using the device.

9 Claims, 12 Drawing Sheets

DEVICE FOR INCUBATING AND WASHING MEMBRANE/GEL AND METHOD USING THEREOF

BACKGROUND

Biological experiments require processing membranes or gels containing biological sample. Biological samples may include deoxyribonucleic acid (DNA), ribonucleic acid (RNA), sugar, lipid, protein, etc. The processing methods may be nucleic acid hybridization, detection using antibodies, and staining, etc. Take Western blot or protein immunoblot as an example, the process includes treating protein-immobilized membrane in steps of blocking, incubating with antibodies, washing, etc., within a set time. In other words, the process puts the membrane sequentially into various agitated liquids/solutions according to a fixed time schedule. Some common requirements for these membrane processing include 1) evenly hybridizing over the membrane and thoroughly washing afterwards; 2) using as little as possible antibodies; and 3) using disposable materials to avoid cross-contamination due to erroneous manual operations.

Technicians often manually perform membrane operations described above. As expected the results may not be repeatable or reliable. Even if some Western Blot processing machines on the market meet the first requirement, i.e., 1) evenly hybridizing over the membrane and thoroughly washing afterwards, most of them failed to meet the latter two requirements, i.e., 2) using as little as possible antibodies; and 3) using disposable materials to avoid cross-contamination due to erroneous manual operations. In addition, high cost may be another factor for the commercially available machines. Consequently, Western blot experiments in the lab are mainly performed manually thirty some years after the invention of the Western blot technique.

SUMMARY

The following embodiments and aspects thereof are described and illustrated in conjunction with devices, systems and methods which are meant to be exemplary and illustrative, not limiting in scope.

The present disclosure provides a device for incubating and washing membrane and gel comprising biological samples.

In one aspect, disclosed herein is a device for incubating or washing a biological sample membrane or gel, the device comprising: (a) a washing cassette; (b) a sample holder disposed within the washing cassette, the sample holder configured to receive a biological sample membrane or gel; (c) a poking gear enclosing partially at least a top portion of the washing cassette, the poking gear configured to poke the sample holder and rotate the sample holder within the washing cassette; and (d) a washing basin assembly configured to hold an incubating or washing liquid and to receive the washing cassette.

In some embodiments, the washing cassette comprises: (a) a front panel; (b) a back panel; (c) a curved top panel connecting the front panel and the back panel; (d) a left frame connecting the front panel, the curved top panel, and the back panel; and (e) a right frame connecting the front panel, the curved top panel, and the back panel; wherein a bottom edge of the front panel, a bottom edge of the back panel, a lower portion of the left fame, and a lower portion of the right frame define an opening, wherein each of the front panel and the back panel comprises one or more orifices, wherein an internal surface of the washing cassette comprises a plurality of protruding strips.

In some embodiments, the poking gear is a poking gear cover comprising: (a) an outer shell; (b) a reset spring disposed inside the outer shell and installed on an internal surface of the outer shell; and (c) a plurality of poking teeth disposed on the internal surface of the outer shell, wherein each poking tooth comprises a hooking side and a smooth side, wherein each poking tooth is configured to reach into the sample holder and clamp to the sample holder via the hooking side.

In some embodiments, the poking gear is a rotating gear cover comprising one or more rotating gears, wherein each rotating gear is configured to reach into the sample holder and poke the sample holder.

In some embodiments, the washing basin assembly comprises one or more washing basins, wherein each washing basin comprise a concave bottom face configured to receive a bottom portion of the washing cassette; wherein the concave bottom face comprises: (a) a protrusion; or (b) a protruding strip; or (c) a plurality of vertical barriers, each vertical barrier comprising an opening on the lower portion of the vertical barrier.

In some embodiments, a machine is disclosed to comprise the device described above. In some embodiments, the machine further comprises: (a) a first motor configured to move an assembly of the poking gear, the washing cassette, and the sample holder vertically; (b) a second motor configured to move the assembly of the poking gear, the washing cassette, and the sample holder horizontally; and (c) a processor configured to control the first motor and the second motor.

In some embodiments, the device further comprises a mechanical arm configured to move an assembly of the poking gear, the washing cassette, and the sample holder.

In some embodiments, a machine is disclose to comprise the device of claim 1, the machine further comprises: (a) a moving robot configured to move an assembly of the poking gear, the washing cassette, and the sample holder, the moving robot comprising: (i) a motor disposed at a bottom portion of the moving robot, the motor configured to move the poking gear, the washing cassette, and the sample holder horizontally; (ii) another motor disposed at a center portion of the moving robot, the other motor configured to move a top portion of the moving robot vertically; and (iii) a processor disposed at the center portion, the processor configured to control the motor and the other motor.

In some embodiments, the sample holder further comprises an insert, wherein the insert is disposed inside the sample holder, wherein the insert is a sheet folded in a shape of an oval cylinder.

In another aspect, a washing cassette is disclosed for incubating or washing a biological sample membrane or gel, the washing cassette comprising: (a) a front panel; (b) a back panel; (c) a curved top panel connecting the front panel and the back panel; (d) a left frame connecting the front panel, the curved top panel, and the back panel; and (e) a right frame connecting the front panel, the curved top panel, and the back panel; wherein a bottom edge of the front panel, a bottom edge of the back panel, a lower portion of the left fame, and a lower portion of the right frame define an opening, wherein each of the front panel and the back panel comprises one or more orifices, wherein an internal surface of the washing cassette comprises a plurality of protruding strips.

In still another aspect, a method is disclosed for incubating or washing a biological sample membrane or gel, the method comprising: (a) providing a sample assembly comprising a poking gear on top of a washing cassette, wherein a sample holder is disposed inside the washing cassette and a biological sample membrane or gel is disposed inside the sample holder; (b) moving at least a part of the sample assembly into a washing basin; and (c) using the poking gear to rotate the sample holder inside the washing cassette, thereby incubating or washing the biological sample membrane or gel.

In some embodiments, the moving in (b) of the method comprises: (i) moving the sample assembly vertically by a first motor; and (ii) moving the sample assembly horizontally by a second motor. In some embodiments, In some embodiments, the moving in (b) of the method comprises: moving the sample assembly by a moving robot, wherein the moving robot: (i) moves the sample assembly horizontally by a motor disposed at a bottom portion of the moving robot; and (ii) moves a top portion of the moving robot vertically by another motor disposed at a center portion of the moving robot. In some embodiments, the poking gear is a poking gear cover comprises: (i) an outer shell; (ii) a reset spring disposed inside the outer shell and installed on an internal surface of the outer shell; and (iii) a plurality of poking teeth disposed on the internal surface of the outer shell, wherein each poking tooth comprises a hooking side and a smooth side, wherein, in (c), the reset spring forces a fraction of the plurality of poking teeth to reach into the sample holder and clamp to the sample holder via the hooking side, thereby rotating the sample holder in a distorted circular fashion within the washing cassette. In some embodiments, the method further comprises: in (c), the reset spring forces the sample holder to slide over the smooth sides of another fraction of the plurality of poking teeth. In some embodiments, the poking gear is a rotating gear cover comprising one or more rotating gears. In some embodiments, the method further comprises: in (c), the plurality of rotating gear reaches into the sample holder and rotates the sample holder in a distorted circular fashion within the washing cassette. In some embodiments, the method further comprises: in (c), at a first time, contacting a fraction of a surface of the biological sample membrane or gel with a solution disposed in the washing basin. In some embodiments, in (c), at the first time, another fraction of the surface of the biological sample membrane or gel is not in contact with the solution disposed in the washing basin. In some embodiments, the method further comprising: in (c), at a second time, contacting a different fraction of the surface of the biological sample membrane or gel with the solution disposed in the washing basin.

Further areas of applicability of the present disclosure will become apparent from the detailed description provided hereinafter. It should be understood that the detailed description and specific examples, while indicating various embodiments, are intended for purposes of illustration only and are not intended to limit the scope of the disclosure.

BRIEF DESCRIPTION OF THE DRAWINGS

The object and features of the present disclosure can be more fully understood and better appreciated with reference to the attached drawings, which are schematic representations only and not necessarily drawn to scale, wherein.

DETAILED DESCRIPTION

The present disclosure relates to an improved apparatus and methods for processing biological samples using automation. Various modifications to the disclosed embodiment will be readily apparent to those skilled in the art and the principles herein may be applied to other embodiments and combination thereof. Although various components are discussed in the context of a particular initial design, it should be understood that the various elements can be altered and even replaced or omitted to permit other designs and functionality. Thus, the present disclosure is not intended to be limited to the embodiments shown but is to be accorded the widest scope consistent with the principles and features described herein. As used herein, the "present disclosure" or "present application" refers to any one of the embodiments of the disclosure described herein, and any equivalents thereof. Furthermore, reference to various feature(s) of the "present disclosure" or "present application" throughout this document does not mean that all claimed embodiments or methods must include the referenced feature(s).

NUMERALS

1 Washing cassette
1.1 Top panel of the washing cassette
1.2 Side frame of the washing cassette
1.3 Orifice on the washing cassette
2 Sample holder
2.1 Opening of the sample holder
2.2 Protrusion of the sample holder
2.3 Insert of the sample holder
3 Poking gear
3.1 Outer shell of the poking gear cover
3.2 Reset spring of the poking gear cover
3.3 Poking tooth
3.4 Rotating gear
4 Washing basin assembly
4.1 Washing basin
4.2 Protrusion on the bottom surface of the washing basin
4.3 Opening at the vertical barrier of the washing basin
5 Motor for vertical translation
6 Motor for horizontal translation
7 Center beam assembly
7.1 Aperture of the center beam assembly
8 Holding arm
9 Sliding arm disposed within the aperture
10 Moving robot
10.1 Motor for horizontal translation
10.2 Motor for vertical translation
10.3 Mating cavity for the protruding strip of the moving robot
10.4 Protruding strip of the moving robot
10.5 Void for a computer
11 Solvent or liquid container assembly
11.1 Solvent or liquid container
12 Mechanical arm To appreciate the features and advantages of preferred apparatuses and methods in accordance with the present disclosure, the reader is referred to the appended FIGS. 1-21 in conjunction with the following discussion. It is to be understood that the drawings are diagrammatic and schematic representations only and are neither limiting of the scope of the present disclosure nor necessarily drawn to scale.

I. Processing Device

Figure 1:
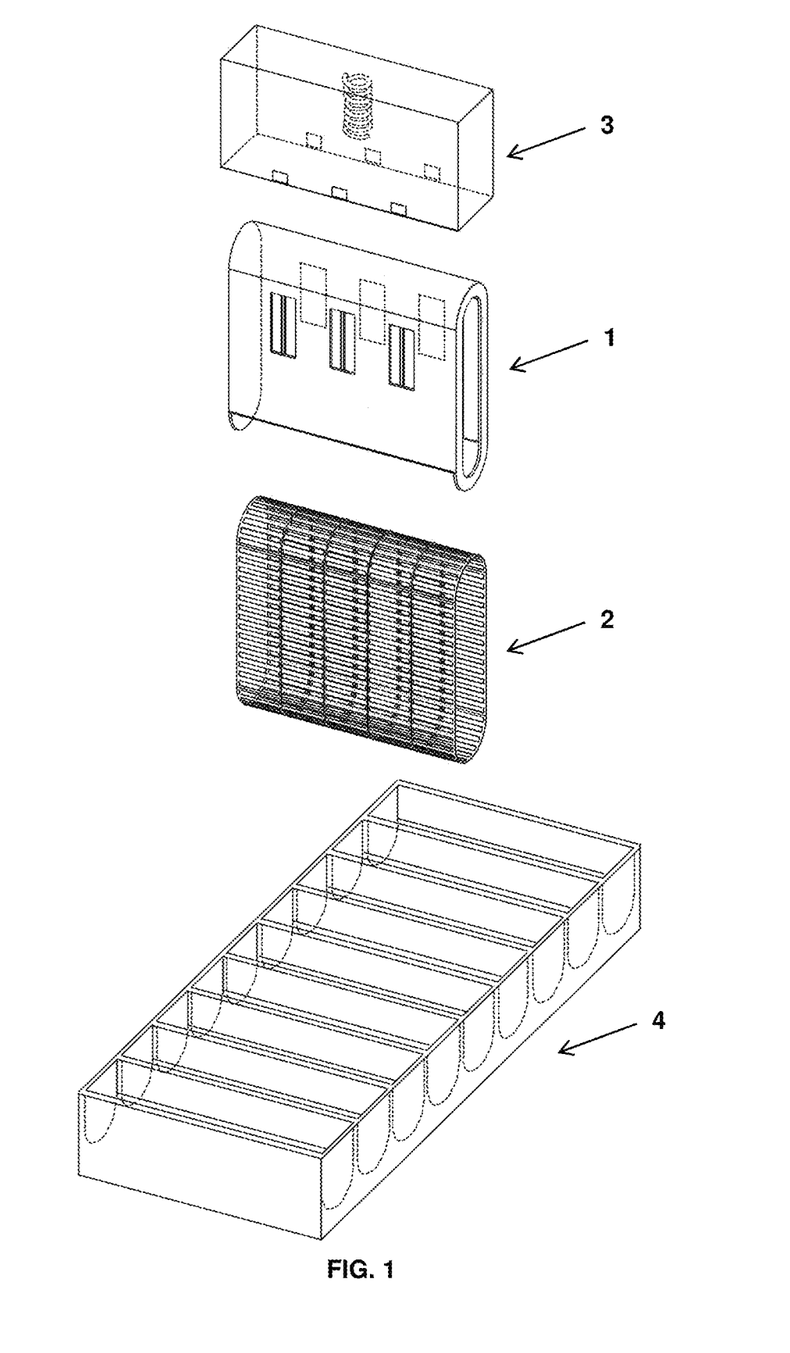
FIG. 1 shows an explosive view of an example device for incubating and washing membrane or gel.

In a first aspect, a device is disclosed for incubating or washing a biological sample membrane or gel. The device can take a variety of forms. As shown in FIG. 1, the device comprises (a) a washing cassette 1; (b) a sample holder 2 disposed within the washing cassette, the sample holder 2 configured to receive a biological sample membrane or gel; (c) a poking gear 3 enclosing partially at least a top portion of the washing cassette 1, the poking gear 3 configured to poke the sample holder 2 and rotate the sample holder within the washing cassette 1; and (d) a washing basin assembly 4 configured to hold an incubating or washing liquid and to receive the washing cassette. In FIG. 1 the poking gear 3 is shown to be a poking gear cover. The poking gear 3 can be a rotating gear cover comprising a rotating gear 3.4 as shown in FIG. 11.

Figure 2:
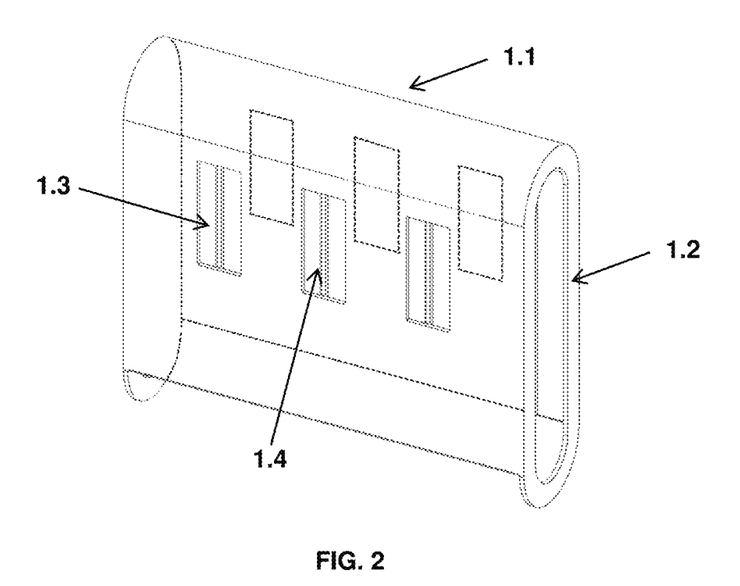
FIG. 2 is an illustration of an example of a washing cassette.
Figure 3:
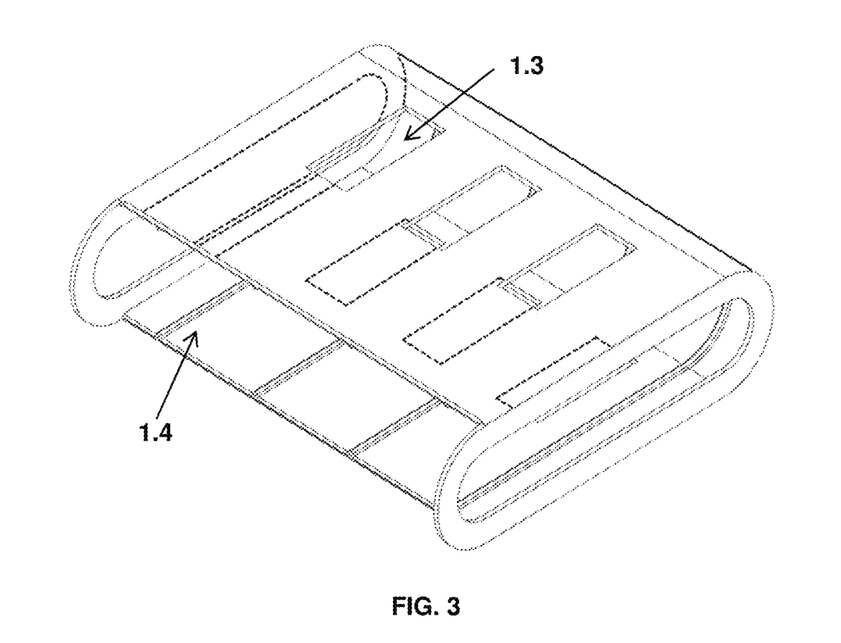
FIG. 3 shows another view of the example of the washing cassette of FIG. 2.

Turning now to FIGS. 2-3, the washing cassette 1 comprises: (a) a front panel; (b) a back panel; (c) a curved top panel 1.1 connecting the front panel and the back panel; (d) a left frame connecting the front panel, the curved top panel 1.1, and the back panel; and (e) a right frame 1.2 connecting the front panel, the curved top panel 1.1, and the back panel; wherein a bottom edge of the front panel, a bottom edge of the back panel, a lower portion of the left fame and a lower portion of the right frame define an opening, wherein the front panel and the back panel comprises a plurality of orifices 1.3, wherein an internal surface of the washing cassette comprises a plurality of protruding strips 1.4. The opening is configured to allow entry of the sample holder into and out of the space enclosed by the washing cassette. The plurality of orifices 1.3 are configured to allow the entry or exit of incubation or washing solutions, etc. The plurality of protruding strips 1.4 are configured to reduce the surface tension which may cause the outer surface of the sample holder adhere to the internal surface of the washing cassette, and may hinder the action of the poking gear to move the sample holder.

Figure 4:
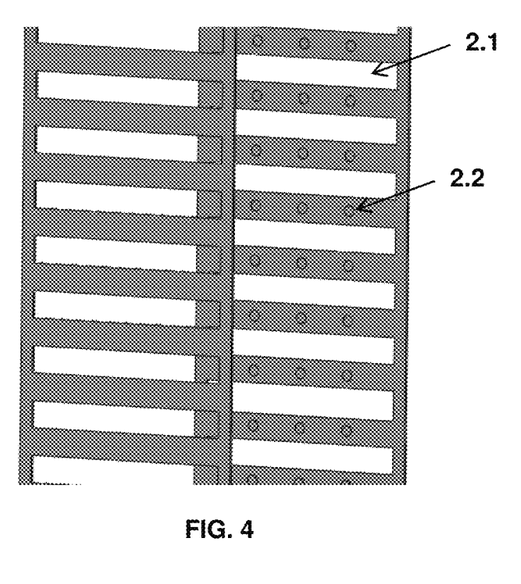
FIG. 4 shows a partial view of an example of a sample holder.

FIG. 4 depicts a partial view of the sample holder 2. The sample holder 2 comprises an oval cylinder comprising a flexible sheet with a plurality of openings 2.1. The flexible sheet can be folded into the oval cylinder with the two opposing ends connected to form the sample holder 2. The plurality of openings 2.1 can provide a contacting point for the poking gear 3 to engage and poke the sample holder 2. The sample holder 2 further comprises a plurality of protrusions 2.2 in the shape of a dot or other forms.

Figure 5:
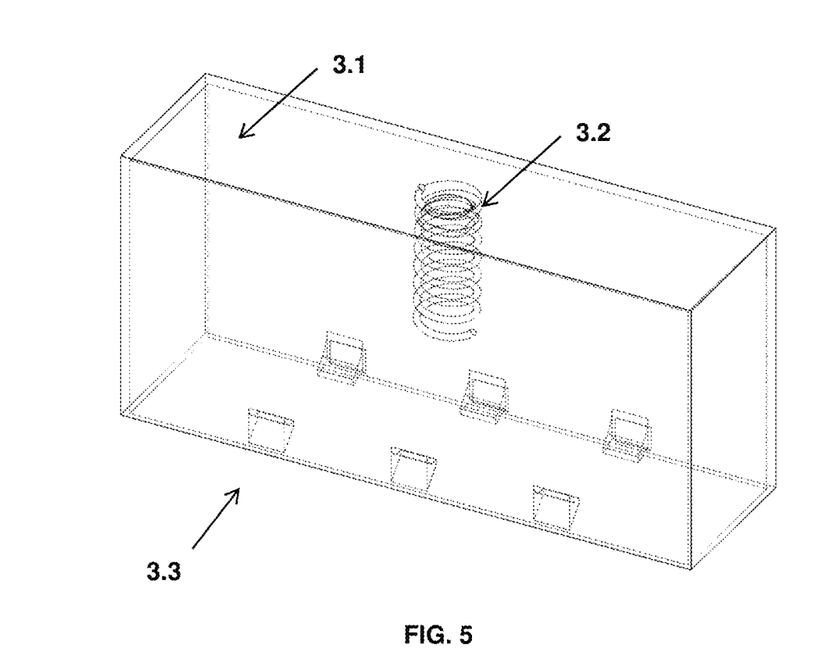
FIG. 5 shows an illustration of an example of a poking gear that is a poking gear cover.
Figure 6:
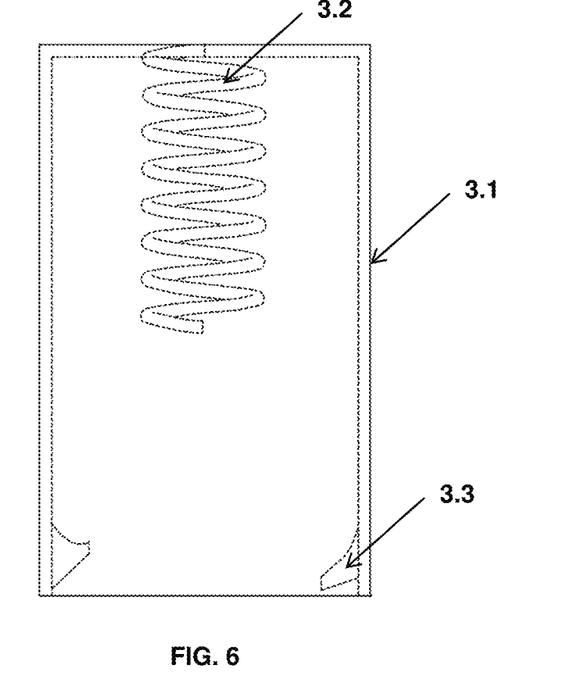
FIG. 6 shows another view of the example of the poking gear cover of FIG. 5.
Figure 7:
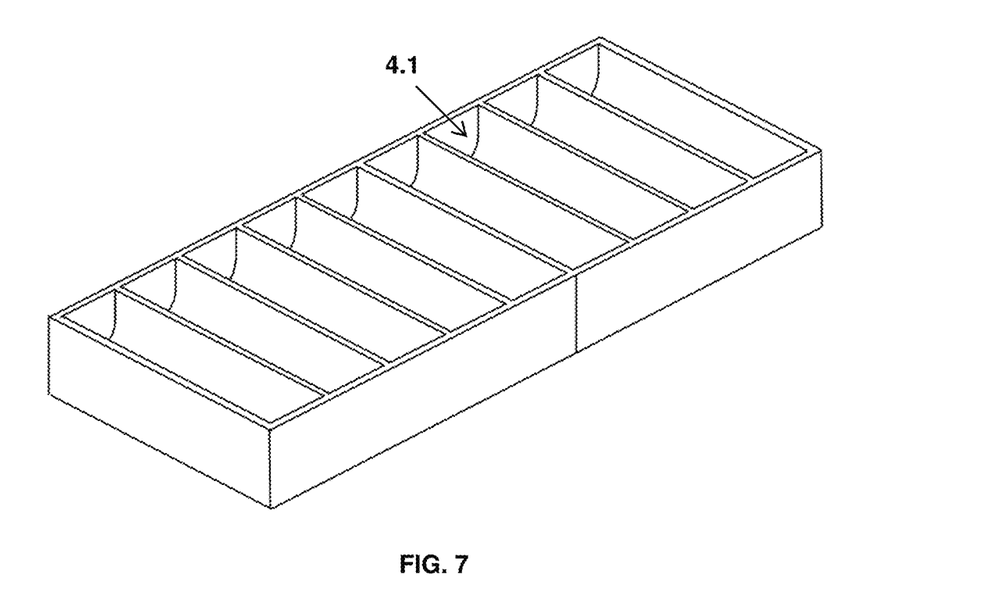
FIG. 7 shows an illustration of an example of a washing basin assembly.
Figure 8:
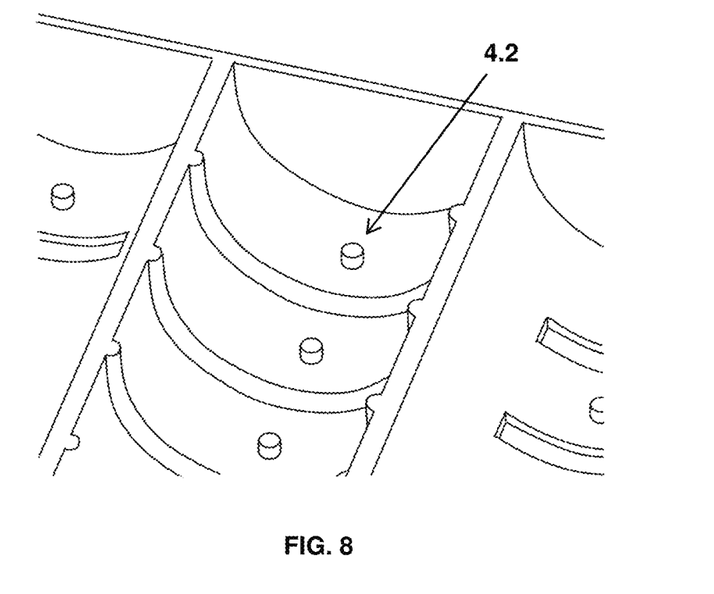
FIG. 8 shows a magnified view of an example of a washing basin assembly showing the bottom surface with a protrusion.
Figure 9:
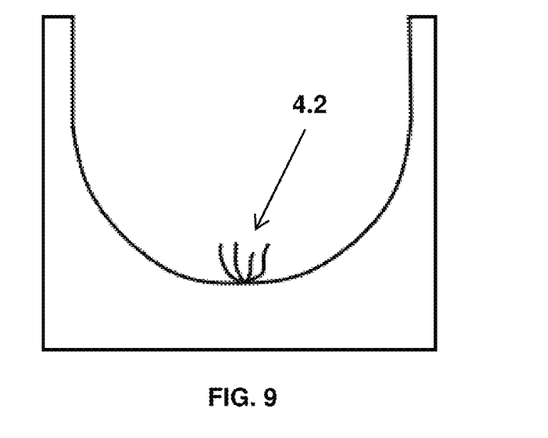
FIG. 9 is shows another example of a washing basin assembly showing a protrusion.
Figure 10:
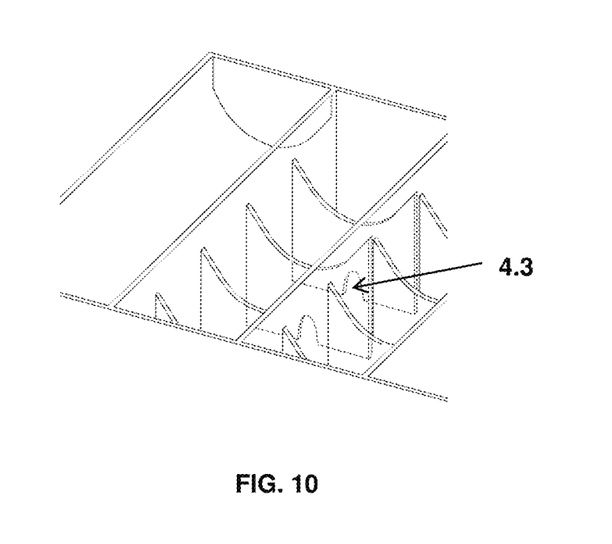
FIG. 10 shows still another example of a washing basin assembly showing a vertical barrier having an opening at the bottom portion.
Figure 11:
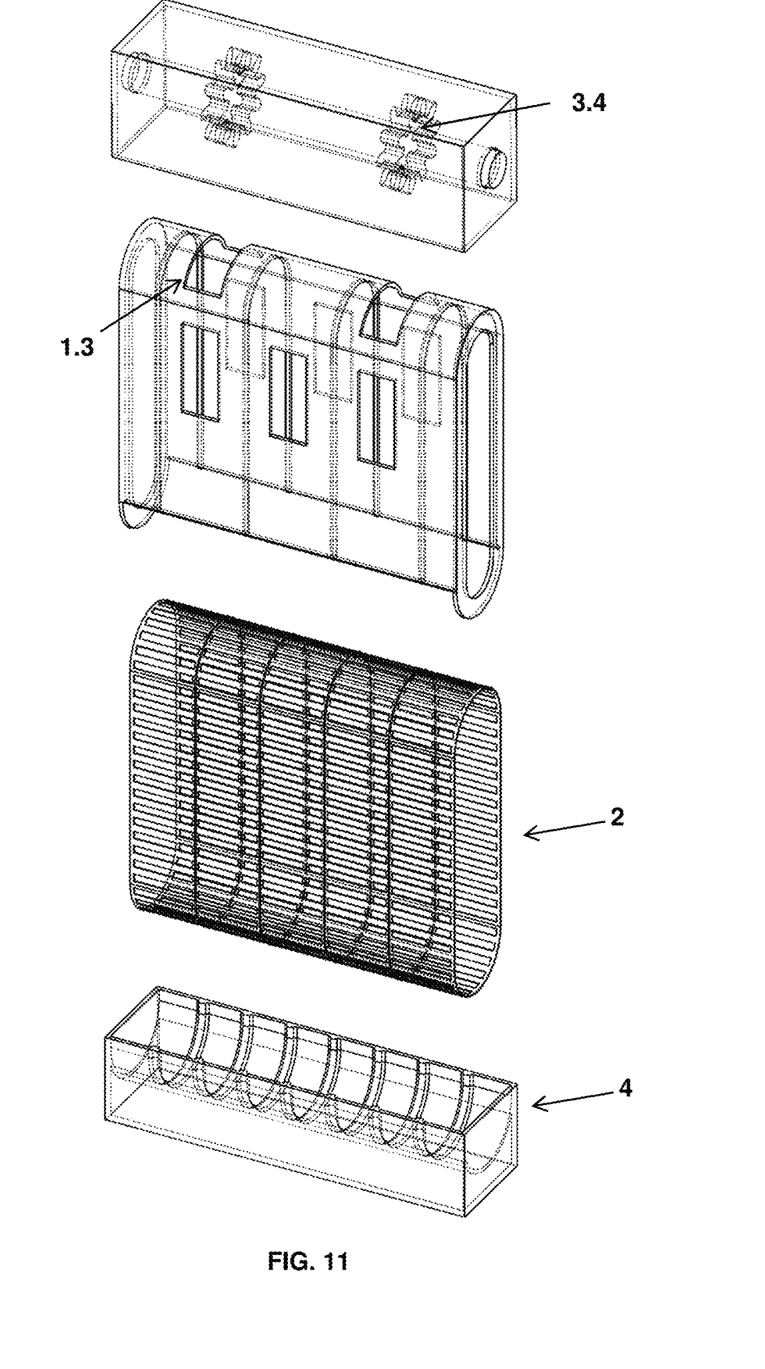
FIG. 11 provides an exploded view of another example device for incubating and washing membrane or gel showing the poking gear is a rotating gear cover.

Turning now to FIGS. 5, 6, and 11, the poking gear 3 can be a poking gear cover or a rotating gear cover. The poking gear cover comprises an outer shell 3.1, a reset spring 3.2 disposed inside the outer shell 3.1 and installed on a top internal surface of the outer shell 3.1, and a plurality of poking teeth 3.3 disposed on the side internal surface of the outer shell 3.1. Each poking tooth 3.3 comprises a hooking side and a smooth side. Each poking tooth 3.3 is configured to reach into the sample holder 2, and clamp to the sample holder 2 via the hooking side. The smooth side of the poking tooth 3.3 can allow the sample holder 2 to slide over the surface of the smooth side. The rotating gear cover comprises one or more rotating gears 3.4. The rotating gear 3.4 is configured to reach into and poke the sample holder 2.

Turning now to FIGS. 7-10, the washing basin assembly 4 can be a rectangular structure with an open top side. The washing basin assembly 4 can comprise a plurality of rectangular washing basin 4.1. The lower portion of the washing basin 4.1 may be a hollow half-cylinder shape. The arc of the curvature of the half-cylinder shape may match the arc of the bottom surface of the washing cassette 1. The lower portion of the washing basin 4.1 may be a smooth surface or may comprise protrusions. For example, the lower portion of the washing basin 4.1 may comprise protrusion 4.2, which can be a strip-shape protrusion, a block-shape protrusion (for example, FIG. 8), or a brush-shape protrusion (for example, FIG. 9). The function of the protrusion 4.2 can be to decrease surface tension. High surface tension may cause the sample holder 2 to stick to the washing cassette 1 and prevent the sample holder 2 from being poked. The lower portion of the washing basin 4.1 may comprise a plurality of barriers, each barrier comprising an opening 4.3 (for example, FIG. 10). The function of the opening 4.3: if there are two or more liquids are used in the washing basin 4.1, the height of the total liquid can be kept the same throughout the washing basin 4.1.

Figure 12:
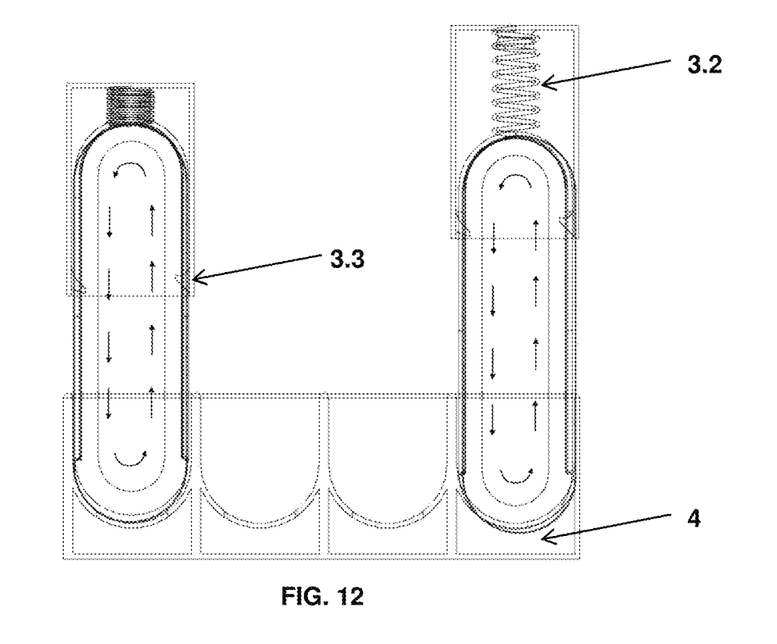
FIG. 12 shows an cartoon of the process to wash or incubate the membrane or gel using the disclosed device.

Turning now to FIGS. 5, 6 and 12, a processing method to use the device for incubating or washing a biological sample membrane or gel is shown. The processing method comprises: assembling the poking gear 3, the washing cassette 1 and the sample holder 2 into a sample assembly; placing the sample assembly into the washing basin assembly 4, using the poking tooth 3.3 or the rotating gear 3.4 to engage the opening 2.1 of the sample holder through the orifice 1.3 on the washing cassette on the surface of sample holder 1; driving the sample holder 2 to slide along the inner surface of the washing cassette 1 via the external force exerted by the poking tooth 3.3 or the rotating gear 3.4 (for example, moving in the direction shown by the arrows in FIG. 12); and rotating the biological sample membrane or gel, which adheres to the inner surface of the sample holder 2, through the incubating/washing solution stored at the low portion of the washing basin 4.1 of the washing basin assembly 4, thereby completing the process of incubating/washing the biological sample or gel.

Figure 13:
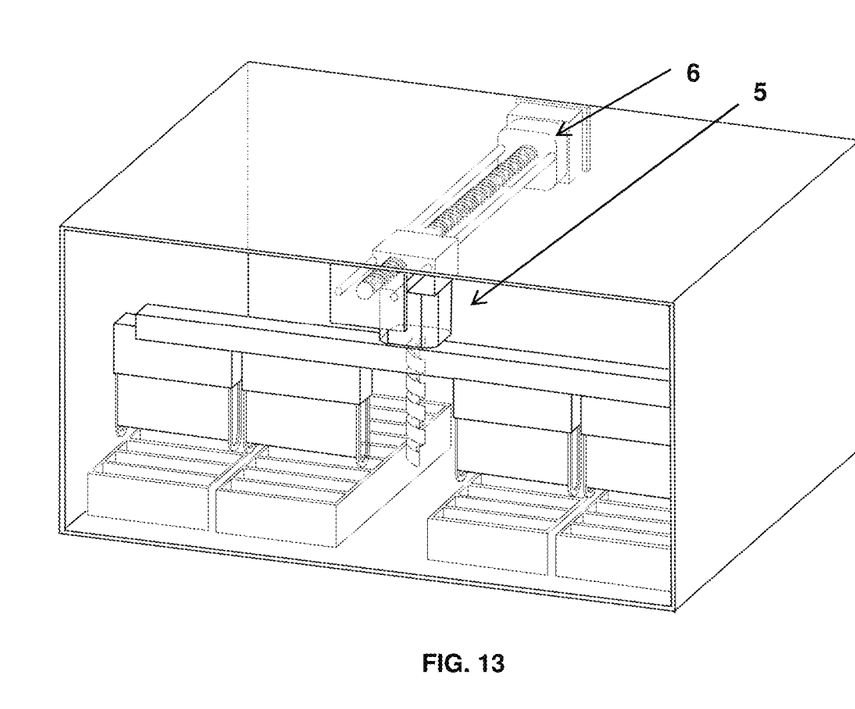
FIG. 13 provides an example machine comprising the device of the present disclosure.
Figure 14:
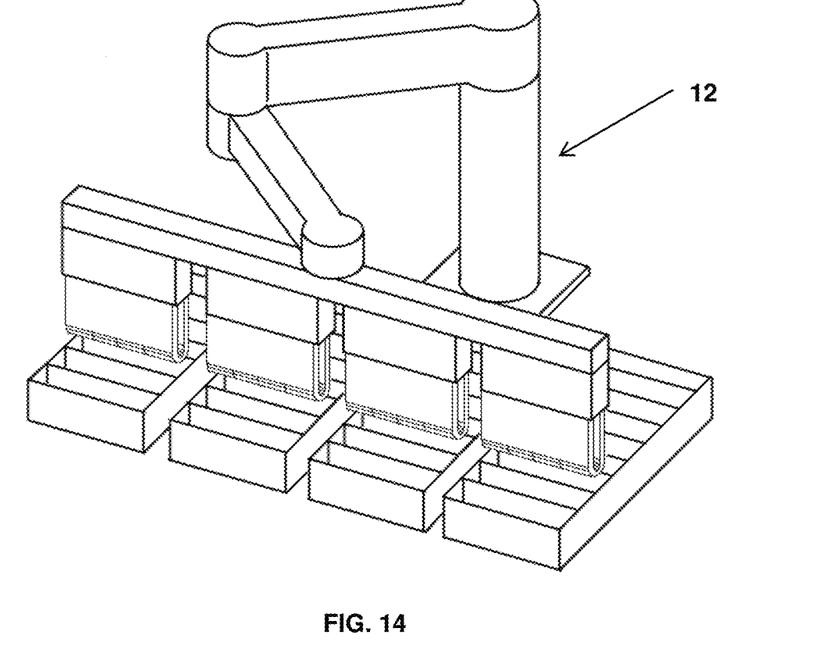
FIG. 14 depicts another example machine comprising the device of the present disclosure.
Figure 15:
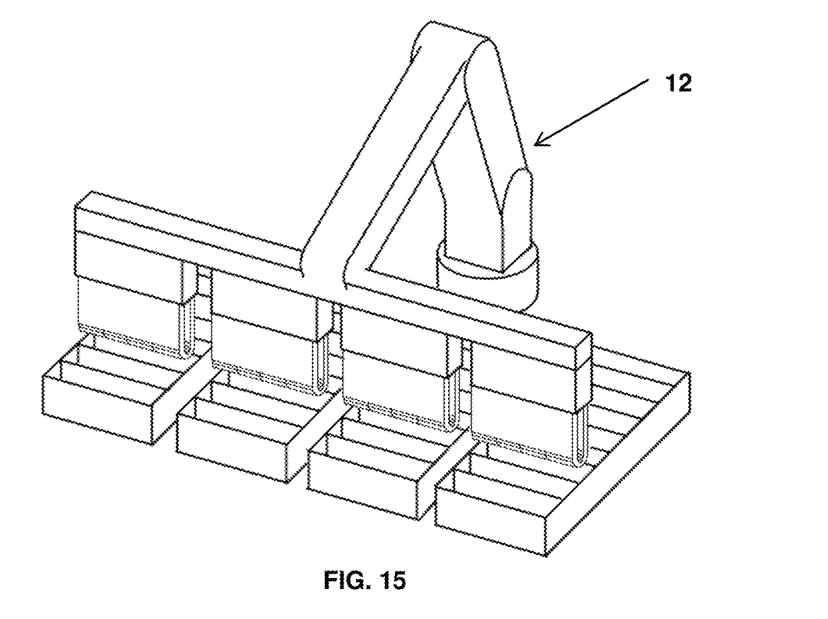
FIG. 15 shows still another example machine comprising the device of the present disclosure.

Turning now to FIGS. 13-15, embodiments of a machine comprising the device for incubating or washing a biological sample membrane or gel are shown. The machine comprises: a computer configured to control the operations of the machine; a motor 5 for vertical translation positioned at the top of the machine; and a motor 6 for horizontal translation positioned at the top of the machine. The motor 5 for vertical translation drives the sample assembly comprising the poking gear 3, the washing cassette 1 and the sample holder 2 so that the sample assembly moves vertically within the washing basin 4.1. The motor 6 for horizontal translation drives the sample assembly comprising the poking gear 3, the washing cassette 1 and the sample holder 2 so that the sample assembly moves horizontally within the washing basin 4.1, thereby completing the process of incubating/washing the biological sample or gel. The afore-mentioned a computer configured to control the operations of the machine; a motor 5 for vertical translation; and a motor 6 for horizontal translation can be replaced by other components including robotic assemblies/arms such as Selective Compliance Assembly Robot Arm (SCARA) or Palletizing robot arm (for example, mechanical arm 12 in FIGS. 14-15) controlled by a computer.

Figure 16:
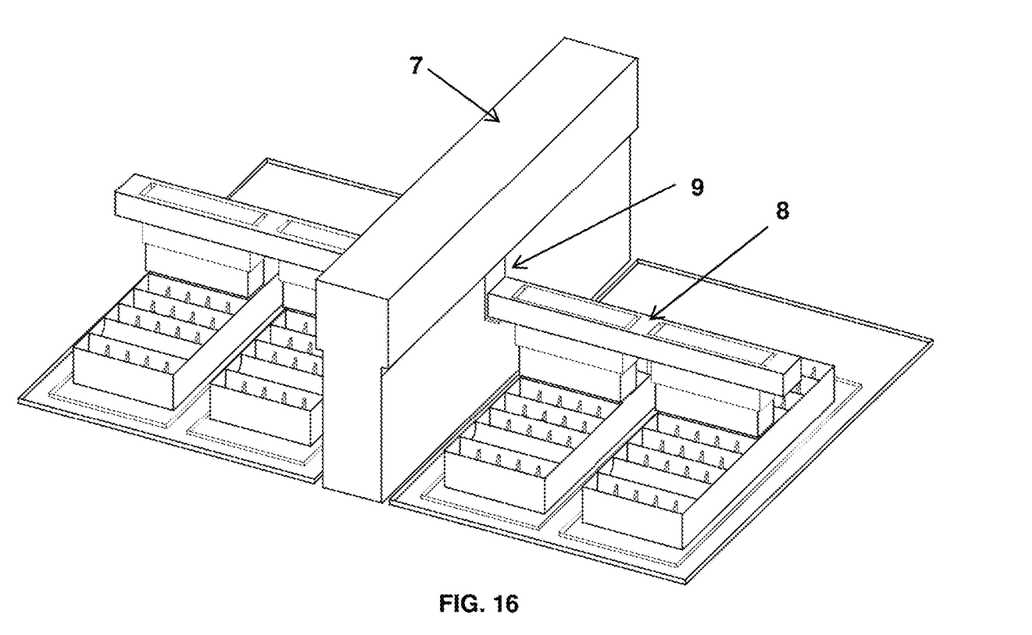
FIG. 16 depicts an example machine comprising the device of the present disclosure.
Figure 17A:
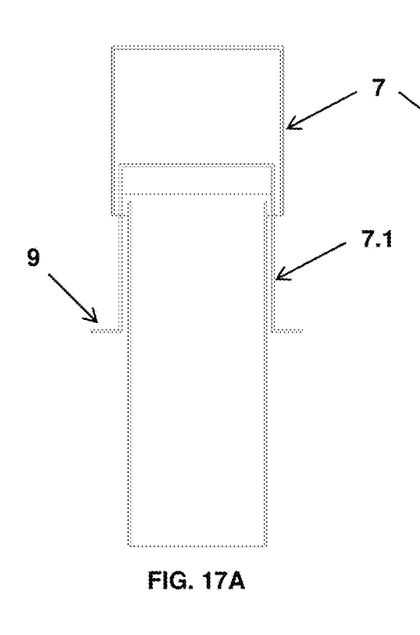
FIGS. 17A and 17B show a cartoon of the example machine in FIG. 16 to translate or move a sample assembly of the present disclosure.
Figure 17B:
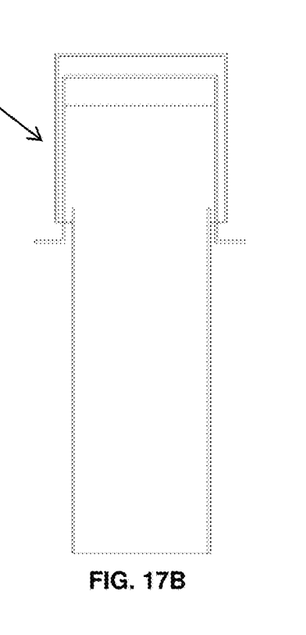

Referring now to FIGS. 16, 17A and 17B, another embodiment for a machine comprising the device for incubating or washing a biological sample membrane or gel is shown. The machine comprises: a center beam assembly 7 positioned at or near the center of the washing basin assembly 4, the center beam assembly 7 comprising an aperture 7.1; a sliding arm 9 whose top portion is positioned within the center beam assembly 7 and whose lower portion protrudes from the aperture 7.1 of the beam assembly 7 and engages with an holding arm 8; and the holding arm 8 drives multiple sample assemblies comprising the poking gear 3, the washing cassette 1 and the sample holder 2. The holding arm 8 is configured to move the sample assemblies vertically within a washing basin 4.1 and horizontally across the surface of the washing basin assembly 4, thereby completing the process of incubating/washing the biological sample or gel. The aperture 7.1 is defined by the top portion and bottom portion of the center beam assembly 7 and allows the sliding arm 9 to move freely vertically and horizontally within the aperture 7.1. The vertical or horizontal movement of the sliding arm 9 can be controlled by one or more motors.

Figure 18:
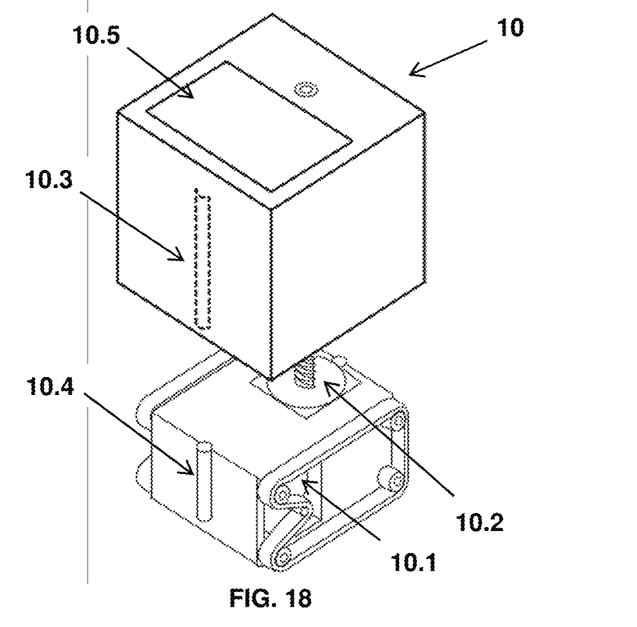
FIG. 18 provides an example of a robot to translate or move the device of the present disclosure.
Figure 19:
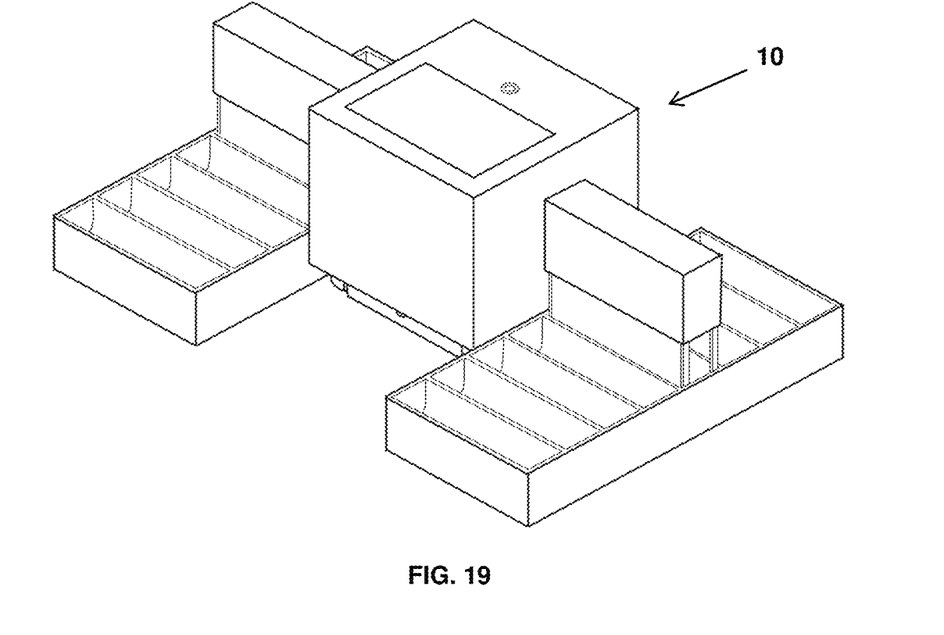
FIG. 19 depicts an example machine using the robot of FIG. 18 to wash and incubate biological sample membrane or gel.

Turning now to FIGS. 18-19, still another embodiment for a machine comprising the device for incubating or washing a biological sample membrane or gel is shown. The machine comprises: a moving robot 10 configured to move vertically and horizontally such that the moving robot 10 drives the sample assembly comprising the poking gear 3, the washing cassette 1 and the sample holder 2 to move vertically and horizontally, thereby completing the process of incubating/washing the biological sample or gel. The moving robot 10 comprises: a motor 10.1 positioned at the lower portion of the moving robot 10 and configured to drive the moving robot 10 forward and backward via the tracks; a motor 10.2 positioned at the lower portion of the moving robot 10 and configured to drive the upper portion of the moving robot 10 upward and downward; a protruding strip 10.4 positioned at the lower portion of the moving robot 10; a mating cavity 10.3 for the protruding strip 10.4 positioned at the upper portion of the moving robot 10 such that when the mating cavity 10.3 and the protruding strip 10.4 are engaged, the upper and lower portions of the moving robot 10 are also engaged; and a void 10.5 configured to hold a computer to control the moving robot 10. The upper portion of the moving robot 10 can connect with and move a sample assembly comprising the poking gear 3, the washing cassette 1 and the sample holder 2 such that the sample assembly can be moved vertically within a washing basin 4.1 and moved horizontally over the washing basin assembly 4, thereby completing the process of incubating/washing the biological sample or gel.

Figure 20:
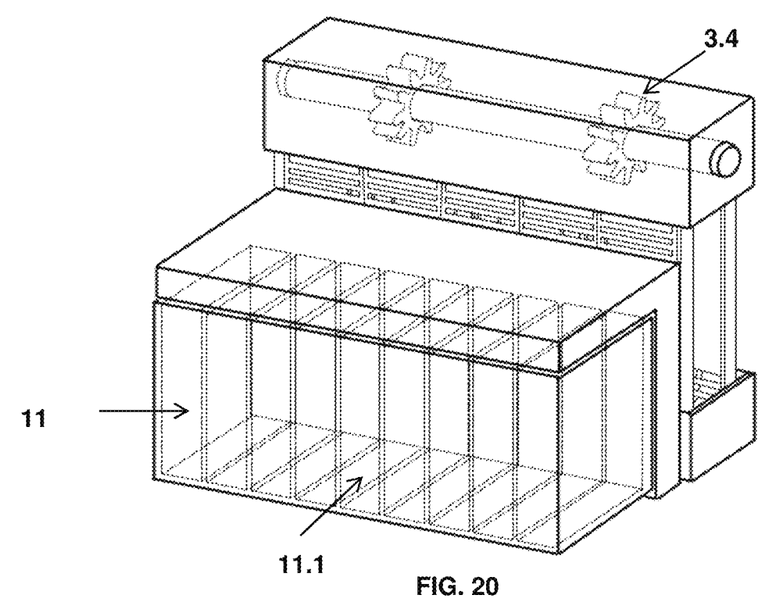
FIG. 20 shows an example solvent/solution containers used in tandem with the device of the present disclosure.

Referring now to FIG. 20, a washing basin 4.1 can engage a solvent/liquid container assembly 11 comprising a plurality of solvent/liquid containers 11.1. By varying the pressure inside the solvent/liquid container 11.1, solvent or liquid within the solvent/liquid container 11.1 can be transferred into or out of the washing basin 4.1 via a conduit between the solvent liquid container 11.1 and the washing basin 4.1 position at the lower portion of the washing basin 4.1, thereby enabling the incubation/washing.

Figure 21:
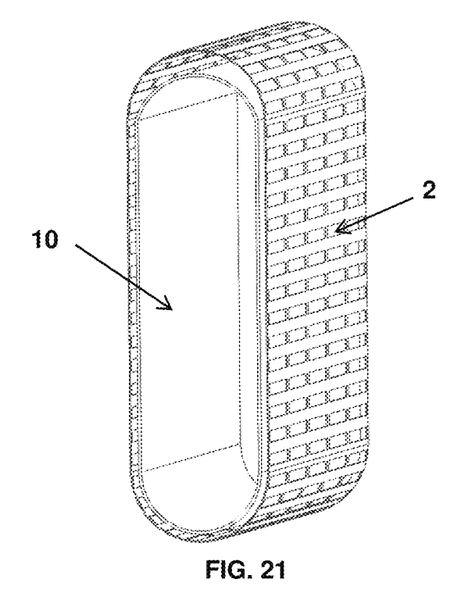
FIG. 21 provides an example of an insert disposed within the sample holder.

Turning now to FIG. 21, in a preferred embodiment, an insert 2.3 can be placed inside a sample holder 2. The insert 2.3 can be made of the same material as that of the sample holder 2. The shape of the insert 2.3 can be a cylinder or an irregular cylinder or a distorted cylinder, which is similar to the shape of the sample holder 2. The insert 2.3 does not comprise any opening. The circumference of the insert 2.3 can be shorter than that of the sample holder 2. The function of the insert 2.3 can be: 1) confining the movable scope of the membrane to be washing between the sample holder 2 and the insert 2.3; and 2) enabling the liquid/solution around the membrane due to the surface tension.

II. Methods of Bioprocessing

In one aspect, the present disclosure also disclose methods of incubating/washing a biological sample membrane or gel, comprising: using a sample assembly comprising the poking gear 3, the washing cassette 1 and the sample holder 2 to move vertically within a washing basin 4.1 and mover horizontally over a washing basin assembly 4, thereby completing the process of incubating/washing the biological sample or gel.

In some cases, the sample assembly may comprise a plurality of poking teeth 3.3 on the poking gear 3. The biological sample membrane or gel may adhere to the inner surface of the sample holder. A poking tooth 3.3 on the poking gear 3 may engage the opening 2.1 on the sample holder 2 via the opening 1.3 on the washing cassette 1. Under the external force exerted onto the poking gear 3, the outer shell 3.1 of the poking gear cover may move downward to compress the reset spring 3.2 of the poking gear cover, which, in turn, press down the washing cassette. The poking tooth 3.3 (see FIG. 12, the left panel, the poking tooth 3.3 on the left side), when moving downward together with the poking gear cover, drives the still engaged sample holder 2 downward on the left side while the right side of the sample holder 2 is forced to move upward and slide over the smooth side of the poking tooth 3.3 on the right side of the poking gear cover, thereby moving the sample holder 2 (together with the biological sample membrane or gel) in an irregular or distorted circular fashion within the washing basin 4.1. When the external force is removed, the compressed reset spring 3.2 of the poking gear cover is reset such that the poking gear cover move upward (see FIG. 12A). At the same time, the poking tooth 3.3 on the right side of the poking gear cover (see FIG. 12B) may engage and move upward the right side of the sample holder 2 while the left side of the sample holder 2 may slide downward over the smooth surface of the poking tooth 3.3 on the left side of the poking gear cover. Accordingly, the biological sample membrane or gel adhered to the inner surface of the sample holder 2 may move together with the sample holder 2 in an irregular or distorted circular fashion within the washing basin 4.1, thereby passing through the incubating/washing liquid/solution at the lower portion of the washing basin 4.1 repeatedly to complete the process of incubating/washing the biological sample or gel.

In some cases, the method may use a sample assembly comprising a poking gear 3 comprising a plurality of rotating gear 3.4 (see, for example, FIG. 11). A motor may drive the rotating gear 3.4 to poke and move the sample holder 2 via the opening 1.3 on the washing cassette 1 in a similar fashion as described above when using a plurality of poking teeth 3.3.

In some cases, the method may use dual motors on the upper portion of a machine to conduct incubating and washing. For example, under the control of a computer, motor 6 for horizontal translation and motor 5 for vertical translation (see, for example, FIG. 13) may drive a sample assembly comprising the poking gear 3, the washing cassette 1 and the sample holder 2 to move vertically within a washing basin 4.1 and move the sample assembly horizontally over a washing basin assembly 4, thereby completing the process of incubating/washing the biological sample or gel.

In some cases, the method may use a center beam assembly 7 to incubate/wash biological sample membrane or gel. For example, under the control of a computer, a motor or motors positioned inside the center beam assembly 7 drive the sliding arm 9 disposed within the aperture 7.1 of the center beam assembly such that the sliding arm 9 controls a sample assembly comprising the poking gear 3, the washing cassette 1 and the sample holder 2 to move vertically within a washing basin 4.1 and mover horizontally over a washing basin assembly 4, thereby completing the process of incubating/washing the biological sample or gel. The aperture 7.1 is defined by the top portion and bottom portion of the center beam assembly 7 and allows the sliding arm 9 to move freely vertically and horizontally within the aperture 7.1. The vertical or horizontal movement of the sliding arm 9 can be controlled by one or more motors. The sliding arm 9 can be saddle-shaped, similar to the Greek capital letter omega. The middle portion (which can be an arc or a bottom-opened block) can slide through the aperture 7.1, and the end hook portions can connect with and control the holding arms, which, in turn, can connect with and control the sample assembly. One advantage of such a configuration is to reduce the chance and the amount of incubating/washing liquid/solution that enters the inside of the device/machine. The chemicals in the incubating/washing liquid/solution may cause the device/machine malfunction during the operation. See FIGS. 16, 17A and 17B.

In some cases, the method may use a mechanical arm 12 and move a sample assembly comprising the poking gear 3, the washing cassette 1 and the sample holder 2 to move vertically within a washing basin 4.1 and mover horizontally over a washing basin assembly 4, thereby completing the process of incubating/washing the biological sample or gel. See FIGS. 14-15.

In some cases, the method may use a moving robot 10 to drive a sample assembly comprising the poking gear 3, the washing cassette 1 and the sample holder 2, and to move the sample assembly vertically within a washing basin 4.1 and horizontally over a washing basin assembly 4, thereby completing the process of incubating/washing the biological sample or gel. For example, a motor 10.1 is positioned at the lower portion of the moving robot 10 and is configured to drive the moving robot 10 forward and backward via the tracks. A motor 10.2 is positioned at the lower portion of the moving robot 10 and is configured to drive the upper portion of the moving robot 10 upward and downward. A protruding strip 10.4 is positioned at the lower portion of the moving robot 10 while a mating cavity 10.3 for the protruding strip 10.4 is positioned at the upper portion of the moving robot 10 such that when the mating cavity 10.3 and the protruding strip 10.4 are engaged, the upper and lower portions of the moving robot 10 are also engaged. A void 10.5 disposed in the upper portion of the moving robot 10 is configured to hold a computer to control the moving robot 10, including controlling the motors 10.1 and 10.2. See FIGS. 18-19.

In some cases, the device can further comprise a solvent/liquid container assembly 11 in tandem with a washing basin 4.1. For example, when using a rotating gear 3.4, the washing basin 4.1 can engage a solvent/liquid container assembly 11, which comprises a plurality of solvent/liquid containers 11.1. By varying the pressure inside the solvent/liquid container 11.1, solvent or liquid stored within the solvent/liquid container 11.1 can be transferred into the washing basin 4.1 via a conduit between the solvent liquid container 11.1 and the washing basin 4.1. The conduit is positioned at the lower portion of the washing basin 4.1, thereby enabling the incubation/washing. See FIG. 20.

Compared with existing devices and machines, the present disclosure disclose a novel device/machine with the following attributes: 1) evenly incubating/washing the membrane or sample; 2) using as little antibody as possible by rotating the membrane/sample through the incubating/washing solution/liquid; and 3) presenting or reducing cross contamination.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention.

We claim:

1. A device for incubating or washing a biological sample membrane or gel, the device comprising:
   (a) a washing cassette;
   (b) a sample holder disposed within the washing cassette, the sample holder configured to receive a biological sample membrane or gel;
   (c) a poking gear enclosing partially at least a top portion of the washing cassette, the poking gear configured to poke the sample holder and rotate the sample holder within the washing cassette; and
   (d) a washing basin assembly configured to hold an incubating or washing liquid and to receive the washing cassette.

2. The device of claim 1, wherein the washing cassette comprises:
   (a) a front panel;
   (b) a back panel;
   (c) a curved top panel connecting the front panel and the back panel;
   (d) a left frame connecting the front panel, the curved top panel, and the back panel; and
   (e) a right frame connecting the front panel, the curved top panel, and the back panel;
   wherein a bottom edge of the front panel, a bottom edge of the back panel, a lower portion of the left fame, and a lower portion of the right frame define an opening, wherein each of the front panel and the back panel comprises one or more orifices, wherein an internal surface of the washing cassette comprises a plurality of protruding strips.

3. The device of claim 1, wherein the poking gear is a poking gear cover comprising:
   (a) an outer shell;
   (b) a reset spring disposed inside the outer shell and installed on an internal surface of the outer shell; and
   (c) a plurality of poking teeth disposed on the internal surface of the outer shell, wherein each poking tooth comprises a hooking side and a smooth side, wherein each poking tooth is configured to reach into the sample holder and clamp to the sample holder via the hooking side.

4. The device of claim 1, wherein the poking gear is a rotating gear cover comprising one or more rotating gears, wherein each of the one or more rotating gears is configured to reach into the sample holder and poke the sample holder.

5. The device of claim 1, wherein the washing basin assembly comprises one or more washing basins, wherein each washing basin comprise a concave bottom face configured to receive a bottom portion of the washing cassette; wherein the concave bottom face comprises:
   (a) a protrusion; or
   (b) a protruding strip; or
   (c) a plurality of vertical barriers, each vertical barrier comprising an opening on the lower portion of the vertical barrier.

6. The device of claim 1, wherein the sample holder further comprises an insert, wherein the insert is disposed inside the sample holder, wherein the insert is a sheet folded in a shape of an oval cylinder.

7. A machine comprising the device of claim 1, the machine further comprises:
   (a) a first motor configured to move an assembly of the poking gear, the washing cassette, and the sample holder vertically;
   (b) a second motor configured to move the assembly of the poking gear, the washing cassette, and the sample holder horizontally; and
   (c) a processor configured to control the first motor and the second motor.

8. A machine comprising the device of claim 1, the machine further comprises a mechanical arm configured to move an assembly of the poking gear, the washing cassette, and the sample holder.

9. A machine comprising the device of claim 1, the machine further comprises:
   (a) a moving robot configured to move an assembly of the poking gear, the washing cassette, and the sample holder, the moving robot comprising:
      (i) a motor disposed at a bottom portion of the moving robot, the motor configured to move the poking gear, the washing cassette, and the sample holder horizontally;
      (ii) another motor disposed at a center portion of the moving robot, the other motor configured to move a top portion of the moving robot vertically; and
      (iii) a processor disposed at the center portion, the processor configured to control the motor and the other motor.

* * * * *